US012642613B2

(12) United States Patent
Zeccola et al.

(10) Patent No.: US 12,642,613 B2
(45) Date of Patent: Jun. 2, 2026

(54) SYSTEM OF OPERATING SURGICAL ROBOTIC SYSTEMS WITH ACCESS PORTS OF VARYING LENGTH

(71) Applicant: Covidien LP, Mansfield, MA (US)

(72) Inventors: Andrew W. Zeccola, Salem, MA (US); Jared N. Farlow, Los Angeles, CA (US); Jaimeen V. Kapadia, Cambridge, MA (US); Paul M. Loschak, Somerville, MA (US); Alok Agrawal, New Haven, CT (US); Gregory A. Dierksen, Arlington, MA (US); Sanjay Jonnavithula, New York, NY (US); Colin H. Murphy, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 41 days.

(21) Appl. No.: 18/686,580

(22) PCT Filed: Sep. 27, 2022

(86) PCT No.: PCT/US2022/044822
§ 371 (c)(1),
(2) Date: Feb. 26, 2024

(87) PCT Pub. No.: WO2023/049489
PCT Pub. Date: Mar. 30, 2023

(65) Prior Publication Data
US 2024/0374330 A1      Nov. 14, 2024

Related U.S. Application Data

(60) Provisional application No. 63/248,695, filed on Sep. 27, 2021.

(51) Int. Cl.
*A61B 90/00*          (2016.01)
*A61B 17/00*          (2006.01)
(Continued)

(52) U.S. Cl.
CPC .............. *A61B 34/37* (2016.02); *A61B 17/34* (2013.01); *A61B 17/3423* (2013.01);
(Continued)

(58) Field of Classification Search
CPC ..... A61B 34/37; A61B 17/34; A61B 17/3423; A61B 34/25; A61B 34/74; A61B 90/37;
(Continued)

(56) References Cited

U.S. PATENT DOCUMENTS 6,132,368 A     10/2000  Cooper
6,206,903 B1     3/2001  Ramans
(Continued)

FOREIGN PATENT DOCUMENTS

WO        2011060031 A1       5/2011
WO        2018005015 A1       1/2018
(Continued)

OTHER PUBLICATIONS

Meehan et al, "Robotic repair of a bochdalek congenital diaphragmatic hernia in a small neonate: robotic advantages and limitations", Journal of Pediatric Surgery, W. B. Saunders Company, US, vol. 42, No. 10, Oct. 5, 2007 (Oct. 5, 2007), p. 1757-1760, XP022502348.
(Continued)

*Primary Examiner* — Sohana Tanju Khayer
(74) *Attorney, Agent, or Firm* — Carter, DeLuca & Farrell, LLP

(57)          ABSTRACT

A surgical robotic system is configured to enable user confirmation of whether one or more access ports are standard or longer length (e.g., bariatric type access ports). The system includes a surgeon console having one or more hand controllers and a head tracking device configured to detect surgeon's attempt to actuate an end effector of an instrument disposed within the access port. The system prevents actuation of the end effector until the insertion
(Continued)

depth of the instrument is sufficient or the user confirms that the access port is of standard length, e.g., less than a preset length threshold.

20 Claims, 9 Drawing Sheets

(51) Int. Cl.

| | |
|---|---|
| *A61B 17/34* | (2006.01) |
| *A61B 34/00* | (2016.01) |
| *A61B 34/30* | (2016.01) |
| *A61B 34/37* | (2016.01) |
| *B25J 13/06* | (2006.01) |
| *G05B 19/4155* | (2006.01) |
| *G06F 3/01* | (2006.01) |

(52) U.S. Cl.
CPC .............. *A61B 34/25* (2016.02); *A61B 34/74* (2016.02); *A61B 90/37* (2016.02); *B25J 13/06* (2013.01); *G05B 19/4155* (2013.01); *G06F 3/012* (2013.01); *G06F 3/013* (2013.01); *A61B 2017/00216* (2013.01); *A61B 34/30* (2016.02); *A61B 2034/742* (2016.02); *A61B 2090/062* (2016.02); *G05B 2219/40269* (2013.01)

(58) Field of Classification Search
CPC .......... A61B 34/30; A61B 2017/00216; A61B 2034/742; A61B 2090/062; B25J 13/06; G05B 19/4155; G05B 2219/40269; G06F 3/012; G06F 3/013
See application file for complete search history.

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |

(56) References Cited

U.S. PATENT DOCUMENTS

| | | | |
|---|---|---|---|
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,165 B2 | 10/2018 | Power |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |

(56) References Cited

U.S. PATENT DOCUMENTS

| | | | |
|---|---|---|---|
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,242 B2 | 7/2019 | Devengenzo et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Loh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 2012/0069166 A1 | 3/2012 | Kunz | |
| 2012/0083661 A1* | 4/2012 | Rockrohr | A61B 17/3462 604/167.03 |
| 2013/0030408 A1* | 1/2013 | Piferi | A61M 25/007 604/523 |
| 2019/0175062 A1* | 6/2019 | Rafii-Tari | A61B 34/74 |
| 2019/0328469 A1* | 10/2019 | Ando | B25J 13/088 |
| 2020/0078096 A1* | 3/2020 | Barbagli | A61B 34/20 |
| 2020/0078097 A1* | 3/2020 | Gregerson | B25J 9/1666 |
| 2020/0163731 A1* | 5/2020 | Itkowitz | A61B 34/25 |
| 2020/0289223 A1* | 9/2020 | Denlinger | A61B 34/77 |
| 2020/0310529 A1* | 10/2020 | Godina | G06F 3/011 |
| 2020/0405375 A1* | 12/2020 | Shelton, IV | A61B 18/1815 |
| 2020/0405403 A1* | 12/2020 | Shelton, IV | A61B 17/3421 |
| 2020/0405417 A1* | 12/2020 | Shelton, IV | A61B 90/361 |
| 2020/0410899 A1* | 12/2020 | Nowosielski | G09B 23/285 |
| 2021/0215932 A1* | 7/2021 | Mair | G06F 3/0346 |
| 2021/0275263 A1* | 9/2021 | Parrini | A61B 90/361 |
| 2022/0039844 A1* | 2/2022 | Cha | A61B 90/39 |
| 2022/0202442 A1* | 6/2022 | Hsu | A61B 34/10 |
| 2022/0241040 A1* | 8/2022 | Hladio | A61B 17/02 |
| 2022/0273396 A1* | 9/2022 | Bozung | A61B 17/142 |
| 2023/0011907 A1* | 1/2023 | Ghebremeskel | A61F 9/0017 |
| 2023/0054209 A1* | 2/2023 | Roh | A61B 34/76 |
| 2023/0226349 A1* | 7/2023 | Kopera | A61N 1/20 600/300 |
| 2023/0255701 A1* | 8/2023 | Post | A61B 34/30 606/82 |
| 2023/0320794 A1* | 10/2023 | Scholan | A61B 34/30 606/1 |
| 2023/0363830 A1* | 11/2023 | Polchin | A61B 5/7425 |
| 2024/0050154 A1* | 2/2024 | Adebar | A61B 34/10 |

(56)  References Cited

U.S. PATENT DOCUMENTS

| 2024/0099777 A1* | 3/2024 | Moller | ................... | A61B 34/25 |
| 2024/0164838 A1* | 5/2024 | Han | ....................... | A61B 90/37 |

FOREIGN PATENT DOCUMENTS

| WO | 2018034966 A1 | 2/2018 |
| WO | 2019005983 A1 | 1/2019 |

OTHER PUBLICATIONS

International Search Report and Written Opinion of the International Searching Authority issued in corresponding application PCT/US2022/044822 mailed Feb. 14, 2023 (17 pages).

* cited by examiner

SYSTEM OF OPERATING SURGICAL ROBOTIC SYSTEMS WITH ACCESS PORTS OF VARYING LENGTH

CROSS REFERENCE TO RELATED APPLICATIONS

The present application is a U.S. National Stage Application filed under 35 U.S.C. § 371(a) of International Patent Application No. PCT/US2022/044822, filed on Sep. 27, 2022, which claims the benefit of and priority to U.S. Patent Provisional Application No. 63/248,695, filed on Sep. 27, 2021. The entire disclosures of the foregoing applications are incorporated by reference herein.

BACKGROUND

Surgical robotic systems are currently being used in minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Certain surgical robotic systems do not support automatic identification of a type of port/trocar that is attached to each arm, so the systems are not aware of port properties, e.g., length.

SUMMARY

The present disclosure provides a surgical robotic system configured to operate endoscopic instruments inserted through an access port and to operate with access ports of varying lengths. In order to prevent damage to the instrument or the access port, the system prevents actuation of an end effector of the instrument while the end effector is within the access port (e.g., tubular portion). End effector actuation is enabled after a first proximal joint of the end effector is inserted into the patient past a threshold depth. This is done to prevent the instrument from being damaged as well as to prevent damaging the access port. Similarly, during instrument extraction, the system also prevents the user from pulling the instrument through the access port while the instrument is actuated (e.g., the end articulated) to prevent the instrument and the port from being damaged.

In surgery, access ports may have varying lengths. For example, bariatric ports, may be longer than the standard-length ports. Long ports feature the same parts as standard-length ports. The long ports use the same types of port seals and attach to the robot arm by the same port latch. The remote center of motion (RCM) of various length ports is also the same distance from the robot arm. A difference between long ports and standard ports is that the long ports typically feature a few additional centimeters of port length below the RCM (i.e., the portion that extends into the patient). The position of the RCM for the port cannot be changed and thus, the minimum insertion depth before which the instrument clears the port is larger for the bariatric port. This may be problematic for a surgical robotic system that cannot automatically detect the type and/or length of the access port that is installed.

The surgical robotic system according to the present disclosure treats all access ports as bariatric ports (i.e., longer ports) and prevents the user from articulating or otherwise actuating the end effector of the instrument until the instrument is inserted to a depth sufficient to clear the longer port. The system is configured to determine the insertion depth of the instrument and whether the user is controlling the instrument (e.g., moving or actuating the end effector). If the surgeon tries actuating the end effector while the end effector is disposed at an insertion depth between the standard-length port and the longer port, the system outputs an alert on a graphical user interface (GUI) requesting confirmation that a standard-length port is being used and that the instrument has cleared a distal end of the access port. Once the surgeon confirms that the standard-length port is being used the system stores this setting until the access port is undocked from a holder.

According to one aspect of the present disclosure, a surgical robotic system is disclosed. The surgical robotic system includes a robotic arm configured to support an access port and an instrument having an end effector inserted into the access port. The system also includes a surgeon console configured to detect user activity. The system further includes a controller configured to: monitor an insertion distance of the instrument within the access port, analyze the user activity, and prevent actuation of the end effector in response to the user activity while the insertion distance is less than a threshold distance.

Implementations of the above embodiment may include one or more of the following features. According to one aspect of the above embodiment, the surgeon console also may include a hand controller having a gimbal assembly and a finger sensor. The user activity may include contacting the finger sensor and/or rotating the hand controller about the gimbal assembly. The surgeon console may also include a head tracking device configured to detect head position and/or eye direction. The user activity may further include head and/or eye pointing toward the surgeon console.

The surgical robotic system may also include a display. The controller may be further configured to output a confirmation query on the display in response to detection of the user activity and the insertion distance being less than the threshold distance. The display may be a touchscreen, and a response to the confirmation query may include touching the touchscreen. The head tracking device may be configured to detect a head nod as the response to the confirmation query. The controller may be further configured to enable actuation of the end effector in response to a confirmation that a length of the access port is less than the threshold distance.

According to another aspect of the present disclosure, a method for controlling a surgical robotic system is disclosed. The method may include monitoring user activity at a surgeon console; monitoring an insertion distance of an instrument having an end effector into an access port, the instrument and the access port supported by a robotic arm. The method may also include detecting the user activity. The method may further include preventing actuation of the end effector in response to the user activity while the insertion distance is less than a threshold distance.

Implementations of the above embodiment may include one or more of the following features. According to one aspect of the above embodiment, the surgeon console may include a hand controller having a gimbal assembly and a finger sensor. Detecting the user activity may include detecting at least one of contacting the finger sensor or rotating the hand controller about the gimbal assembly. Detecting the user activity may include tracking at least one head position or eye direction at a head tracking device of the surgeon console. Tracking the head position and/or the eye direction may include detecting at least one of head or eye pointing toward the surgeon console. The method may further include displaying a graphical user interface on a display. The method may further include outputting a confirmation query on the display in response to detection of the user activity and the insertion distance being less than the threshold distance. The method may also include receiving a response to the confirmation query at a touchscreen of the display. The method may further include detecting a head nod as the response to the confirmation query at the head tracking device. The method may also include enabling actuation of the end effector at a controller in response to a confirmation that a length of the access port is less than the threshold distance.

According to yet another aspect of the present disclosure, a surgical robotic system is disclosed, which includes a robotic arm configured to support an access port and an instrument having an end effector inserted into the access port. The system also includes a surgeon console having a hand controller configured to control at least one of the robotic arm or the instrument and a display. The system further includes a controller configured to output a first prompt on the display, the first prompt requesting user identification a property of the access port and confirm the property of the access port. The controller is further configured to output a second prompt on the display, the second prompt requesting user affirmation of the property of the access port based on a confirmation of the property of the access port.

Implementations of the above embodiment may include one or more of the following features. According to one aspect of the above embodiment, the property of the access port may be length. The first prompt may include a query requesting user selection of a type of the access port, the type being either standard or long. In confirming the property of the access port, the controller may be further configured to determine whether the instrument is operating outside a virtual boundary. In determining whether the instrument is operating outside a virtual boundary, the controller may be further configured to count a number of operations outside the virtual boundary and duration of the operations outside the virtual boundary.

BRIEF DESCRIPTION OF THE DRAWINGS

Various embodiments of the present disclosure are described herein with reference to the drawings wherein.

DETAILED DESCRIPTION

Figure 1:
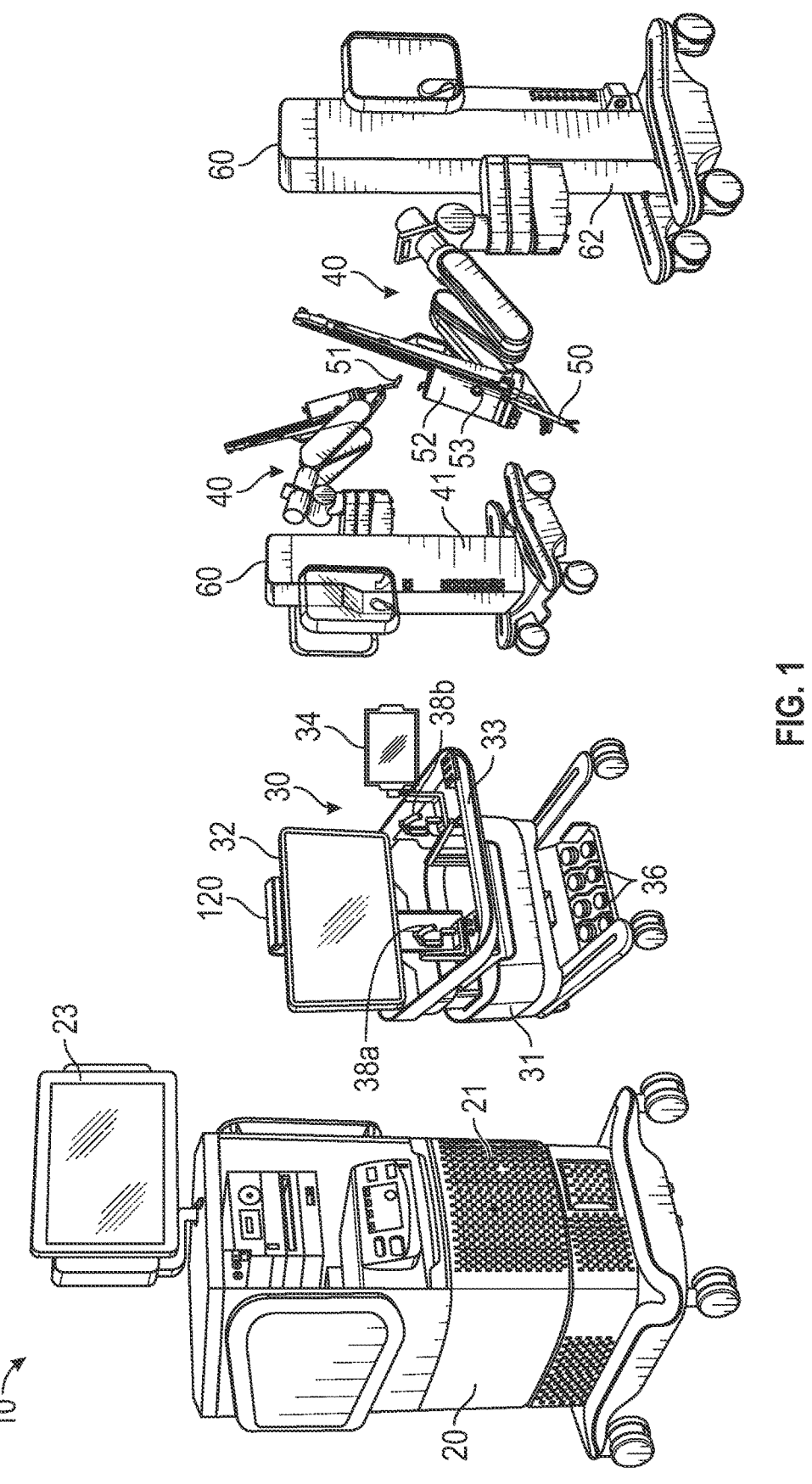
FIG. 1 is a schematic illustration of a surgical robotic system including a control tower, a console, and one or more surgical robotic arms according to an embodiment of the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include a camera 51 configured to capture video of the surgical site. The surgeon console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgeon console 30 also includes a plurality of user interface devices, such as foot pedals 36 and a pair of hand controllers 38a and 38b which are used by a user to remotely control robotic arms 40. The surgeon console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the hand controllers 38a and 38b.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
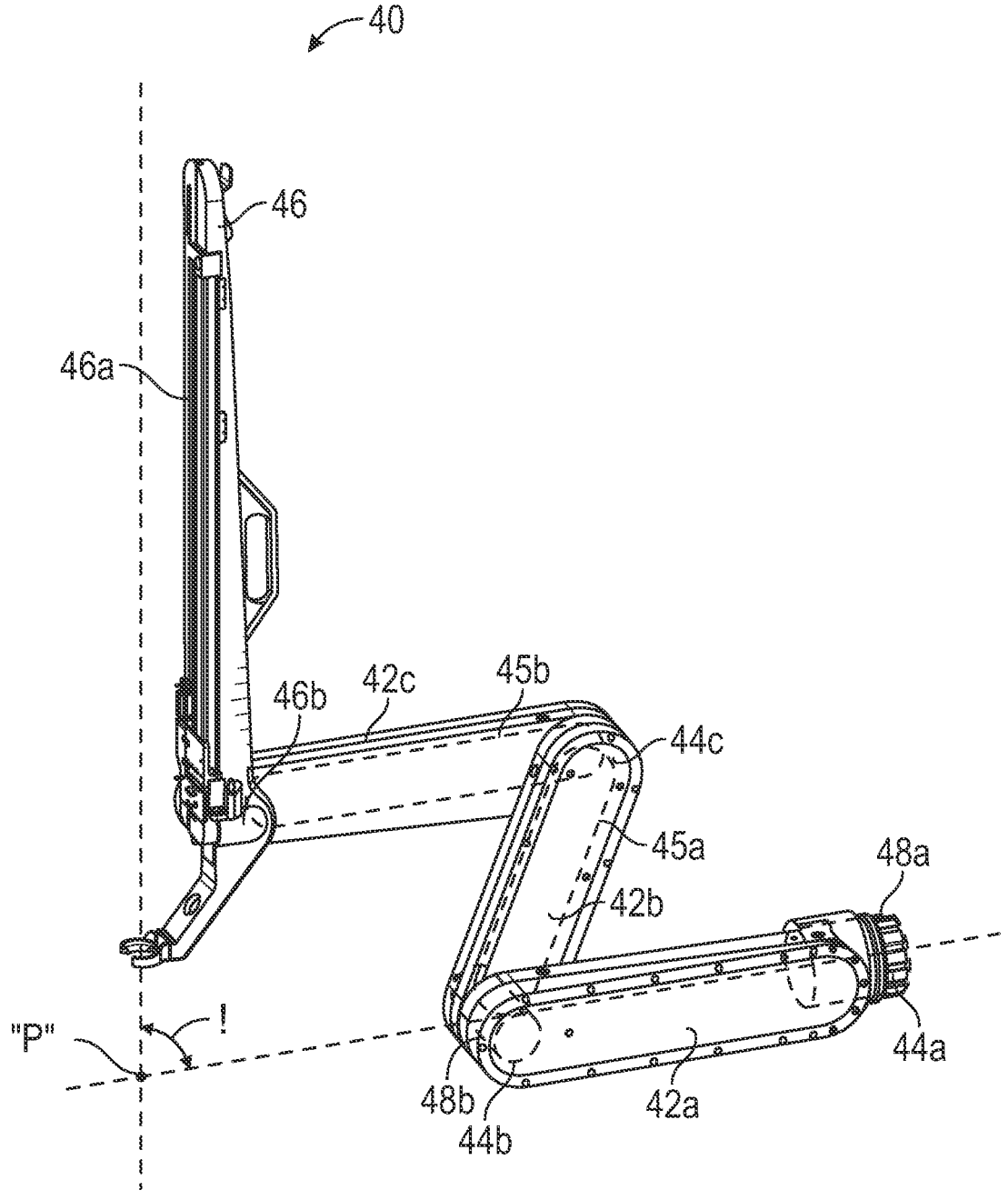
FIG. 2 is a perspective view of a surgical robotic arm of the surgical robotic system of FIG. 1 according to an embodiment of the present disclosure.
Figure 3:
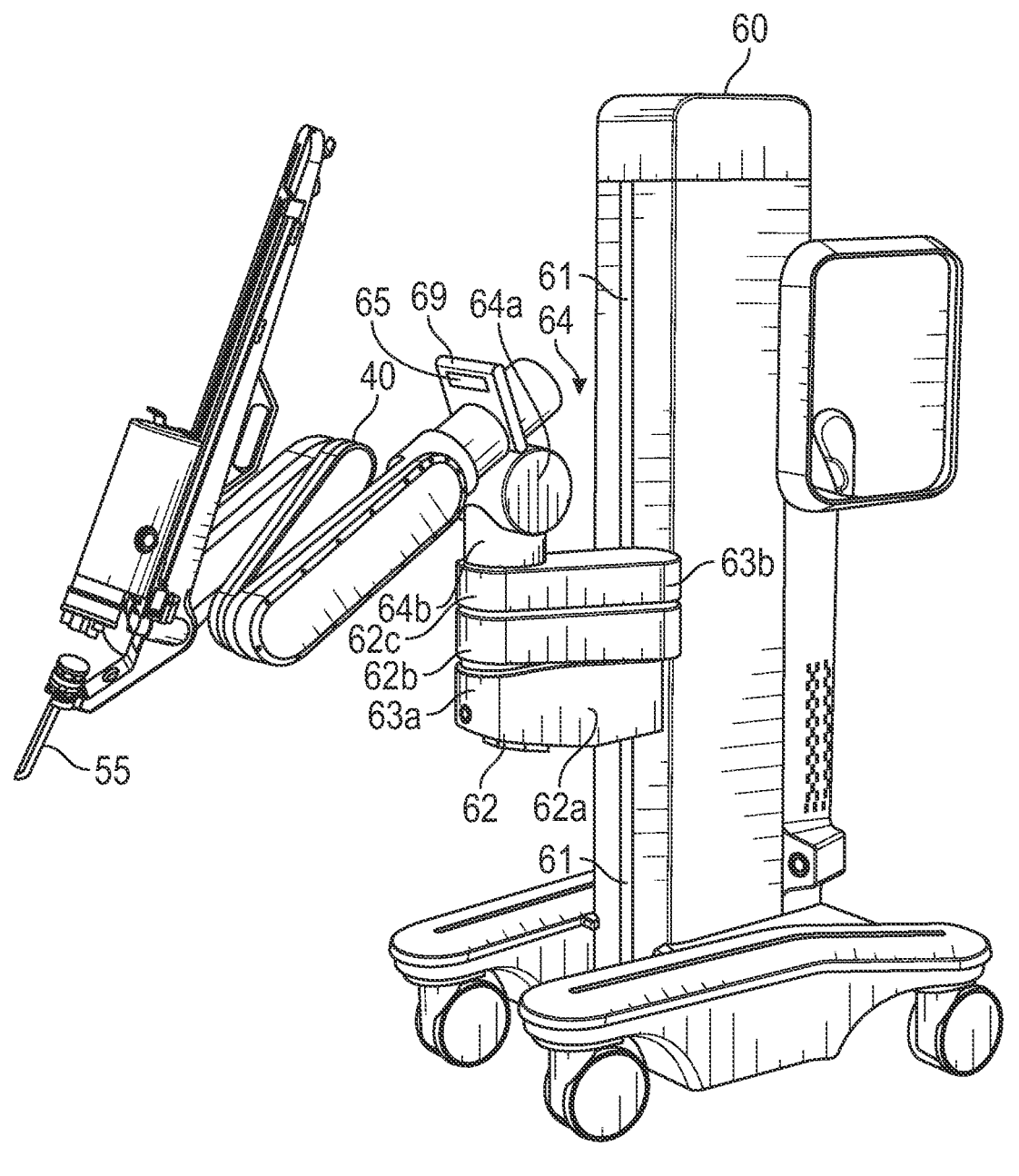
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle $\theta$ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle $\theta$. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic port 55 (FIG. 3) held by the holder 46.

The robotic arm 40 also includes a plurality of manual override buttons 53 (FIG. 1) disposed on the IDU 52 and the setup arm 62, which may be used in a manual mode. The user may press one or more of the buttons 53 to move the component associated with the button 53.

Figure 4:
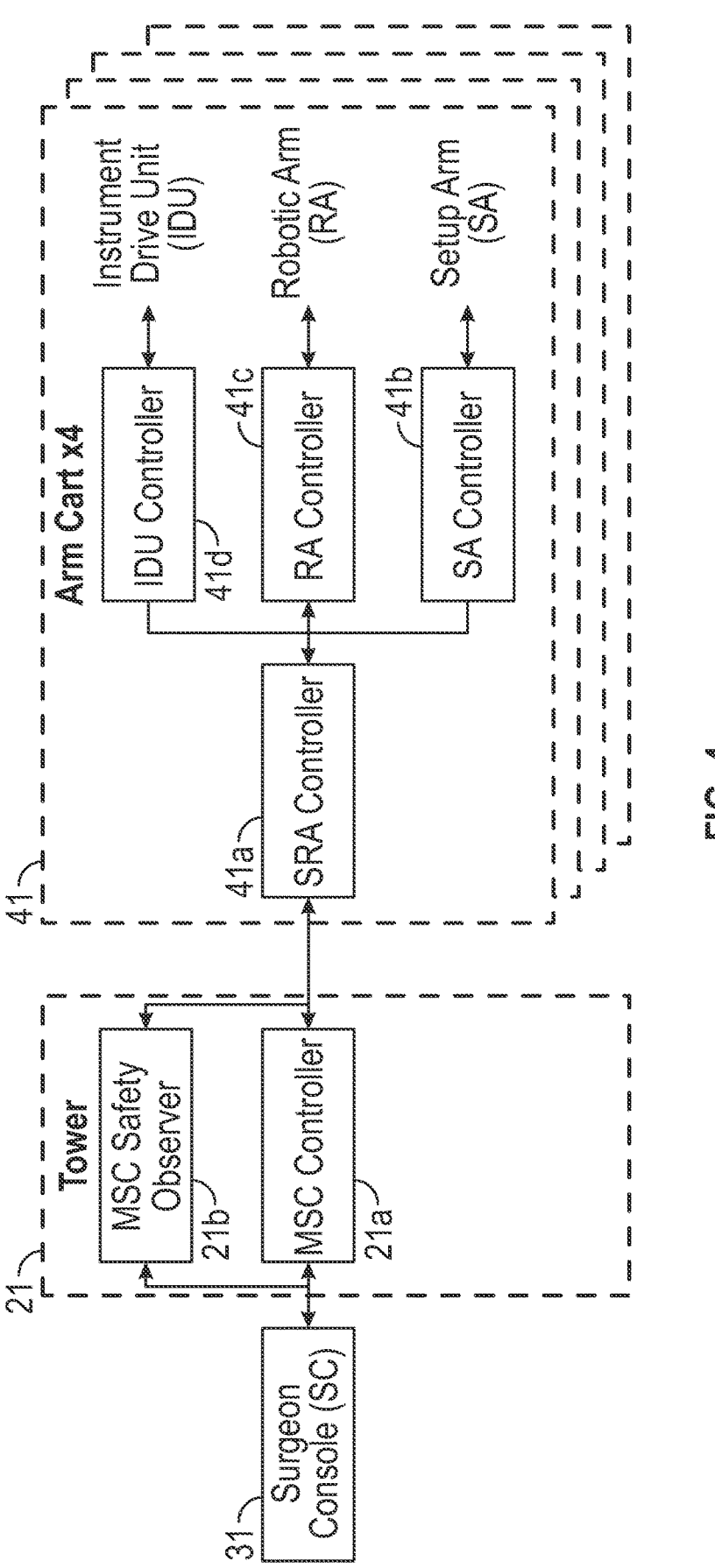
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the hand controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the hand controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the hand controller controlling the robotic arm 40, e.g., the hand controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the hand controller 38a may be embodied as a coordinate position and role-pitch-yaw ("RPY") orientation relative to a coordinate reference frame, which is fixed to the surgeon console 30. The desired pose of the instrument 50 is relative to a fixed frame on the robotic arm 40. The pose of the hand controller 38a is then scaled by a scaling function executed by the controller 21a. In embodiments, the coordinate position is scaled down and the orientation is scaled up by the scaling function. In addition, the controller 21a also executes a clutching function, which disengages the hand controller 38a from the robotic arm 40. In particular, the controller 21a stops transmitting movement commands from the hand controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the hand controller 38a or 38b is then passed by an inverse kinematics function executed by the controller 21a. The inverse kinematics function calculates angles for the joints 44a, 44b, 44c of the robotic arm 40 that achieve the scaled and adjusted pose input by the hand controller 38a or 38b. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
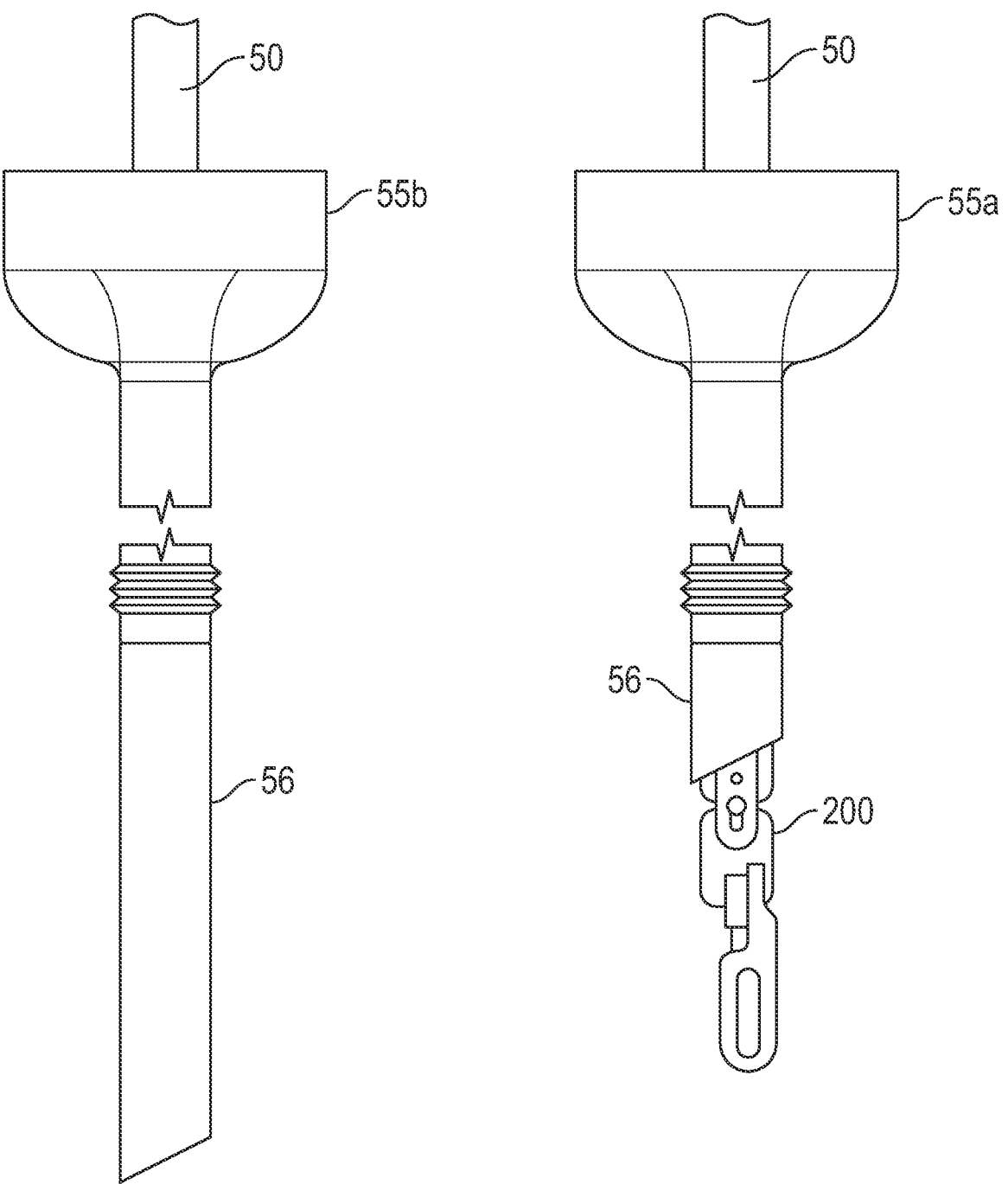
FIG. 5 is a side view of access ports of different lengths according to the present disclosure.

With reference to FIG. 5, during surgery, ports of different lengths may be used, in particular, long ports 55b may be used for bariatric surgery, which are longer than standard ports 55a. Use of longer ports affects the functionality of the system 10 during instrument exchange and position control of the instrument 50 inside the port 55. More specifically, instrument exchange requires the wristed instrument to be straightened and closed during extraction before the first proximal joint reaches the bottom of the port.

During use of the instrument 50, the instrument 50 is inserted into a longitudinal tube 56 of the port 55 by advancing the instrument 50 and the IDU 52 along the sliding mechanism 46a. The instrument 50, and in particular an end effector 200 is advanced to a desired depth. The distance to which the instrument 50, and in particular, the end effector 200 has been advanced is continuously tracked by the IDU controller 41d and other controllers (e.g., controller 21a).

The surgical robotic system 10 is configured to determine whether the user of the surgeon console 30 is attempting to control the instrument 50 and/or end effector 200. Attempts to control the instrument 50 include inputting activation commands through the hand controllers 38a and 38b to actuate the end effector 200 as well as whether the surgeon is facing or engaging with the surgeon console 30. The surgical robotic system 10 utilizes the following hardware of the surgeon console 30 to determine user's intent to control the instrument 50.

With reference to FIG. 1, the surgeon console 30 includes a head tracking device 120, which may include one or more cameras, illuminating devices, such as IR projectors and the like. By way of the tracking device 120, the surgeon console 30 is configured to, in real-time or near real-time, identify and track a user's head and user's eyes. Head position and/or eye direction is used by the controller 31a of the surgeon console 30 to determine whether the user is engaged with, or disengaged from, the surgeon console 30.

Figure 6:
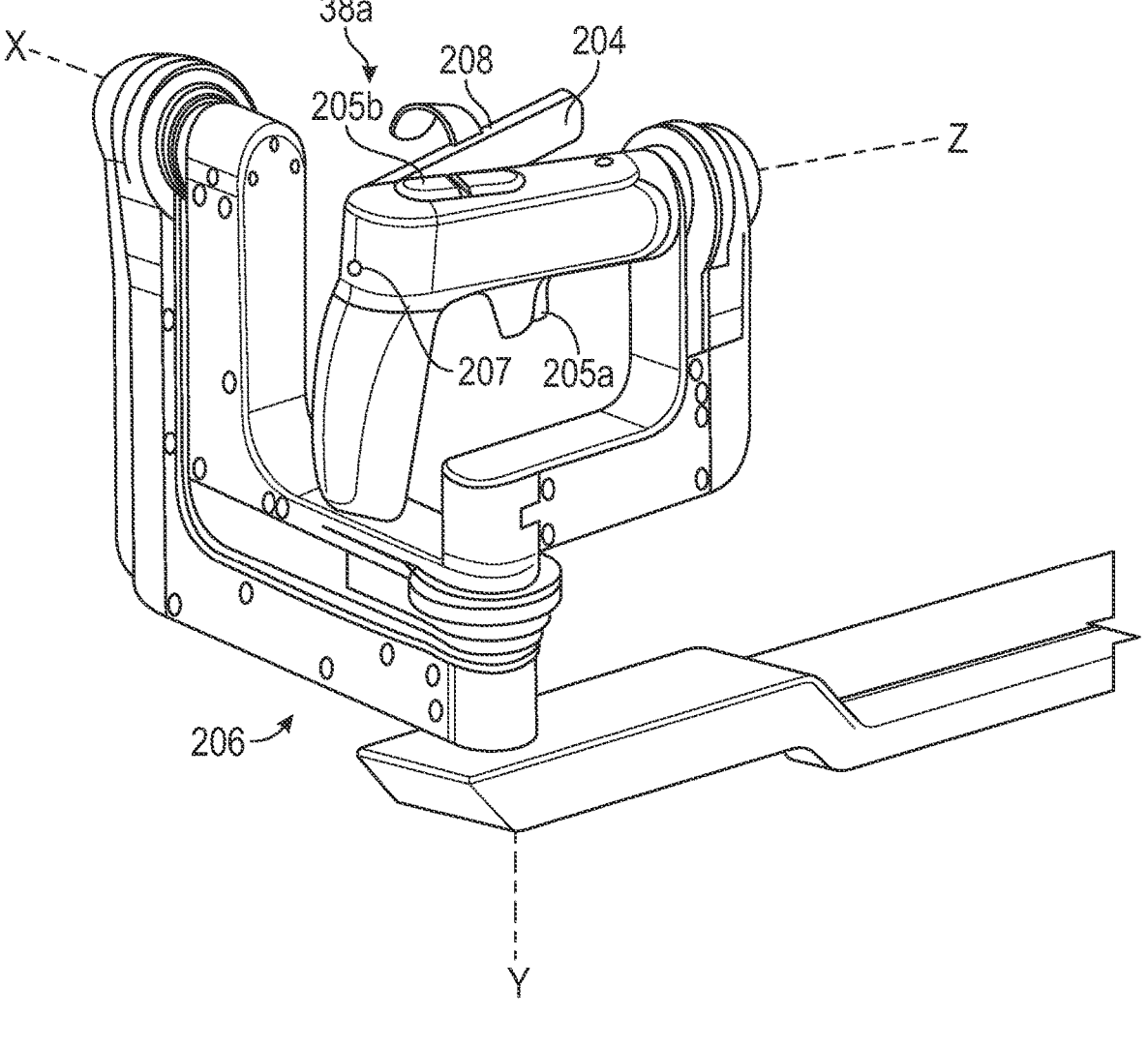
FIG. 6 is an enlarged perspective view of a hand controller of the surgeon console of FIG. 1.

The surgeon console 30 is also configured to track user engagement with the hand controllers 38a and 38b. FIG. 6 shows the right-hand controller 38b, which is a mirror copy of the left-hand controller 38b. Each of the hand controllers 38a and 38b includes a paddle 208 configured controlling actuation of the end effector, e.g., opening and closing jaws of the end effector 200. The paddle 208 may include a finger sensor 204 configured to detect presence or movement of a finger, such as touch sensors, capacitive sensors, optical sensors, and the like. In embodiments, the finger sensor 204 may be disposed on any portion of the hand controllers 38a and 38b. Each of the hand controllers 38a and 38b may also include a trigger 205a and one or more buttons 205b for activating various functions of the instrument 50. In addition, each of the hand controllers 38a and 38b may include a gimbal assembly 206 allowing for movement and rotation of the hand controllers 38a and 38b about three axes (x, y, z). The hand controllers 38a and 38b may also include an infrared proximity sensor 207 configured to detect hand contact with a grip of the hand controllers 38a and 38b. Details of the hand controllers 38a and 38b are provided in U.S. Patent Publication No. 2020/0315729, titled "Control arm assemblies for robotic surgical systems" filed on Nov. 30, 2018, the entire contents of which are incorporated by reference herein.

The controller 31a of the surgeon console 30 monitors user interactions with the hand controllers 38a and 38b and controls the instrument(s) 50 in response to user inputs. In addition, the controller 31a also monitors individual or a new velocity of each joint of the gimbal assembly 206. The controller 31a further monitors displacement of each of the joint of the gimbal assembly 206 and/or net displacement of the gimbal assembly 206. Furthermore, the controller 31a may also monitor the input angle and/or velocity of the paddle 208.

Figure 7:
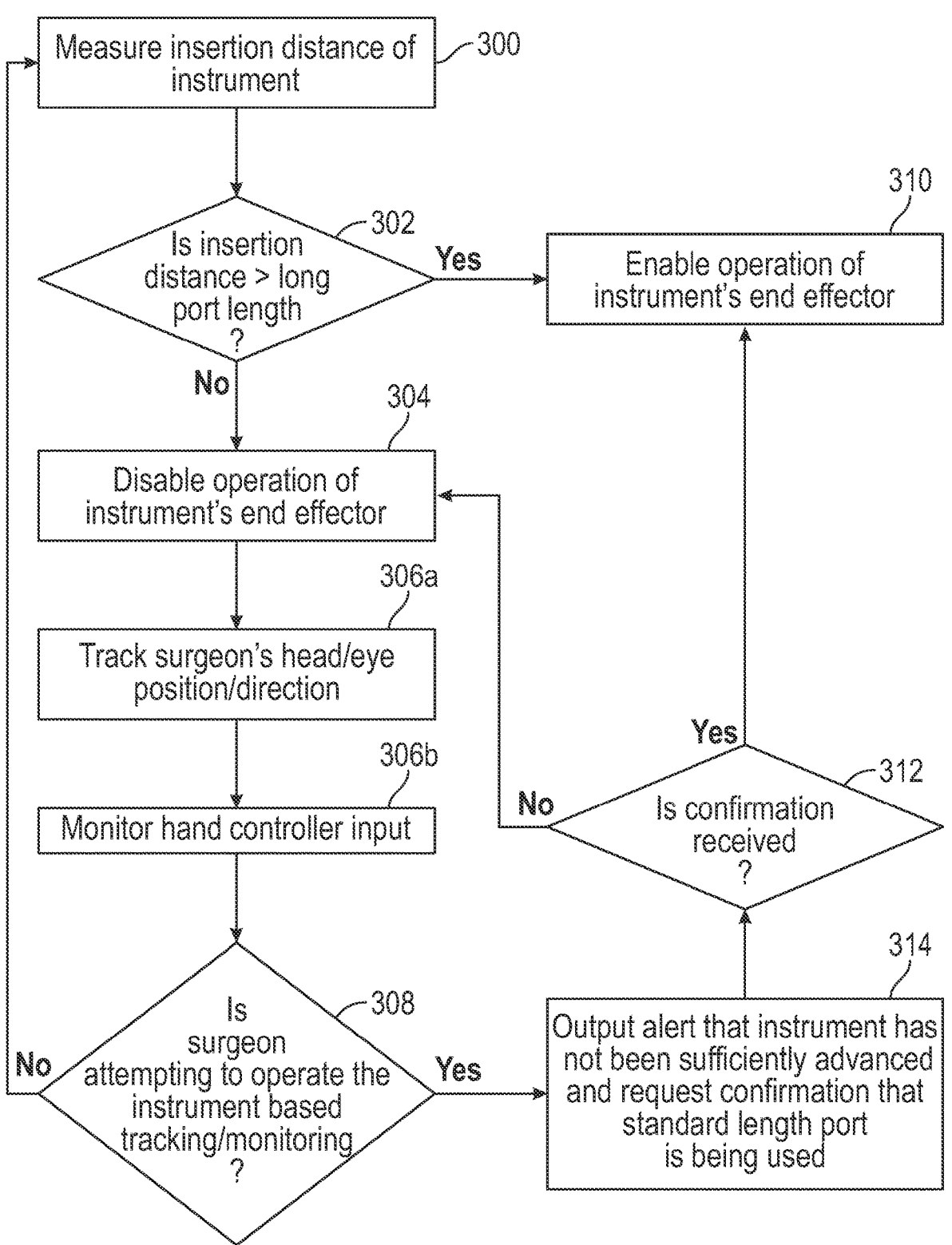
FIG. 7 is a flow chart of a method for controlling the surgical robotic system of FIG. 1 according to one embodiment of the present disclosure.

With reference to FIG. 7, a method for verifying length of the access port 55 includes at step 300 determining (i.e., measuring) the depth of insertion of the instrument 50 into the access port 55. Insertion distance tracking may be determined using encoders or other sensors tracking the sliding mechanism 46a, which is configured to move the IDU 52 along the second longitudinal axis defined by the holder 46. The distance threshold is set to be longer than the length of the long port 55b to ensure safe actuation of the instrument 50 and/or the end effector 200. At step 302, the measured insertion distance is compared a threshold, which corresponds to a length of the long port 55b. If the insertion distance or the depth of the instrument 50 is longer than the length of the long port 55b then the controller 21a allows actuation of the instrument 50 and/or the end effector 200 at step 310.

At step 304, if the insertion distance or the depth of the instrument 50 is less than the length of the long port 55b then the controller 21a prevents actuation of the instrument 50 and/or the end effector 200 by disabling actuation of the instrument 50. Disabling of the instrument 50 may be accomplished by ignoring user input commands from the surgeon console 30 at the IDU 52. While actuation of the instrument 50 is disabled, the controller 31a of the surgeon console 30 monitors user activity as step 306 with respect to the surgeon console 30. User activity includes any interaction by the surgeon with the surgeon console 30. In particular, at step 306a, the controller 31a tracks surgeon's head and eye movement and direction to determine whether the surgeon is looking at the display 32. If the surgeon is looking at the display 32, then it is determined that the surgeon is intending to control the instruments 50.

Additionally or alternatively, at step 306b, the controller 31a may also monitor surgeon's engagement with the hand controllers 38a and 38b by monitoring finger sensors 204, proximity sensors 207, movement of the gimbal assembly 206, pressing trigger 205a or buttons 205b, and/or movement of the paddles 208. If user input of a predetermined type and/or magnitude is detected at step 308, while the insertion distance of the instrument 50 is less than the threshold distance, then the controller 21a outputs an alert at step 314 to the surgeon and/or other staff indicating that the instrument 50 has not been sufficiently advanced and requesting confirmation at step 312 that the standard-length port 55a is being used.

The alert and confirmation query may be output on any of the displays 23, 32, and 34 of the control tower 20 and the surgeon console 30, respectively. Confirmation may be received by touching a corresponding button, e.g., "YES", displayed on any of the displays 23, 32, and 34. The surgeon may also input the confirmation by shaking the head affirmatively (e.g., a vertical nod), which can be tracked by the head tracking device 120. In embodiments, the surgeon may input confirmation by touching the finger sensors 204 using any suitable gesture, such as a double tap, pressing the trigger 205a and/or buttons 205b, etc. Furthermore, the surgeon may press one of the foot pedals 36 of the surgeon console 30 to confirm the access port length. In response to confirmation, the controller 21a may store the confirmation and modify any parameters associated with the confirmation, such as the threshold distance. This would prevent the surgeon reentering confirmation on subsequent uses (i.e., insertion) of the instrument 50.

Once confirmation is received, then the controller 21a enables actuation of the instrument 50 and/or the end effector 200 at step 310 in response to the surgeon's inputs. The method of FIG. 7 may be carried out for each of the access ports 55 held by each of the robotic arms 40 until all of the instruments 50 being used have been activated. In embodiments, another confirmation may be used to apply the same port selection to each of the robotic arms 40 to minimize the number of prompts being displayed.

Figure 8:
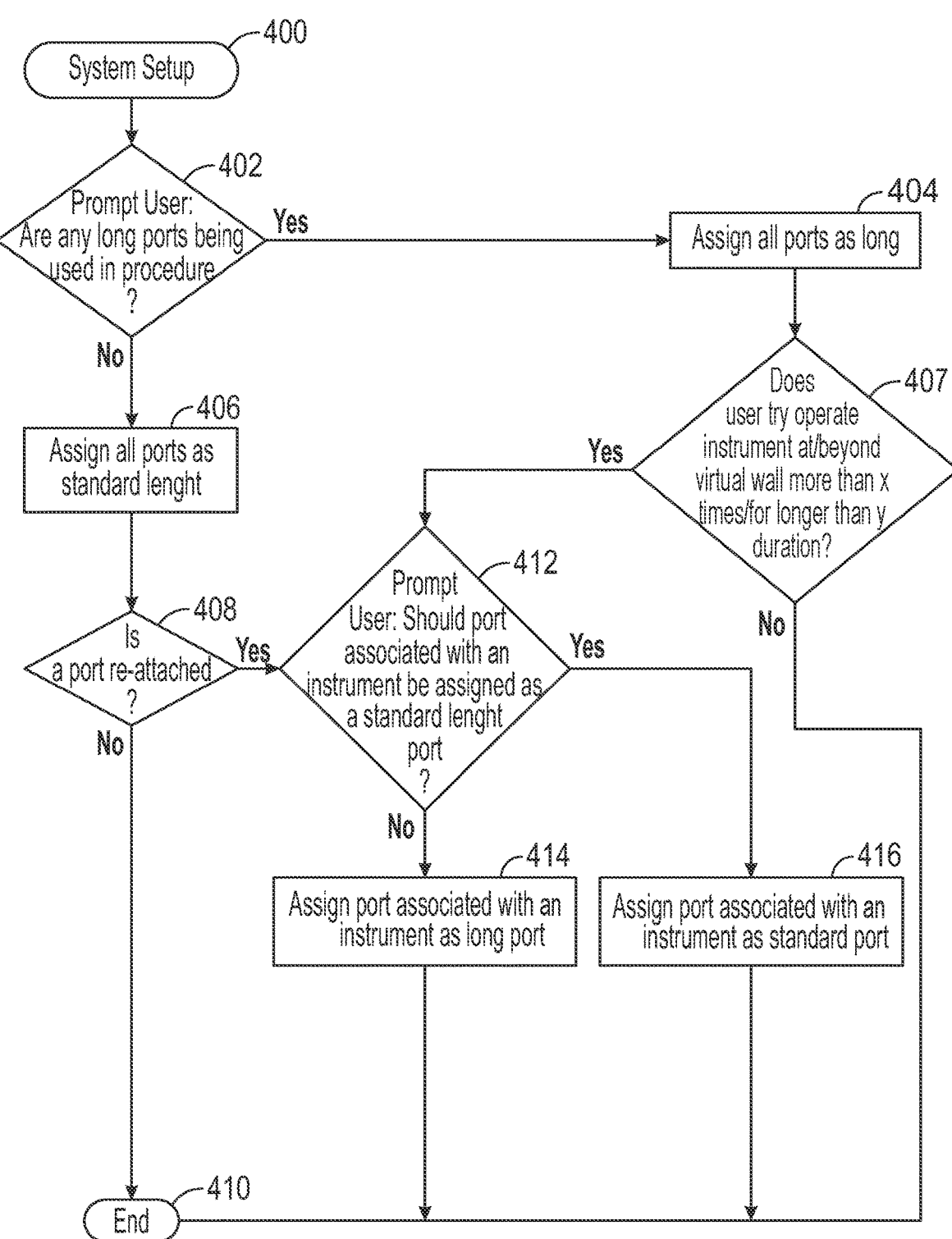
FIG. 8 is a flow chart of a method for controlling the surgical robotic system of FIG. 1 according to another embodiment of the present disclosure.
Figure 9:
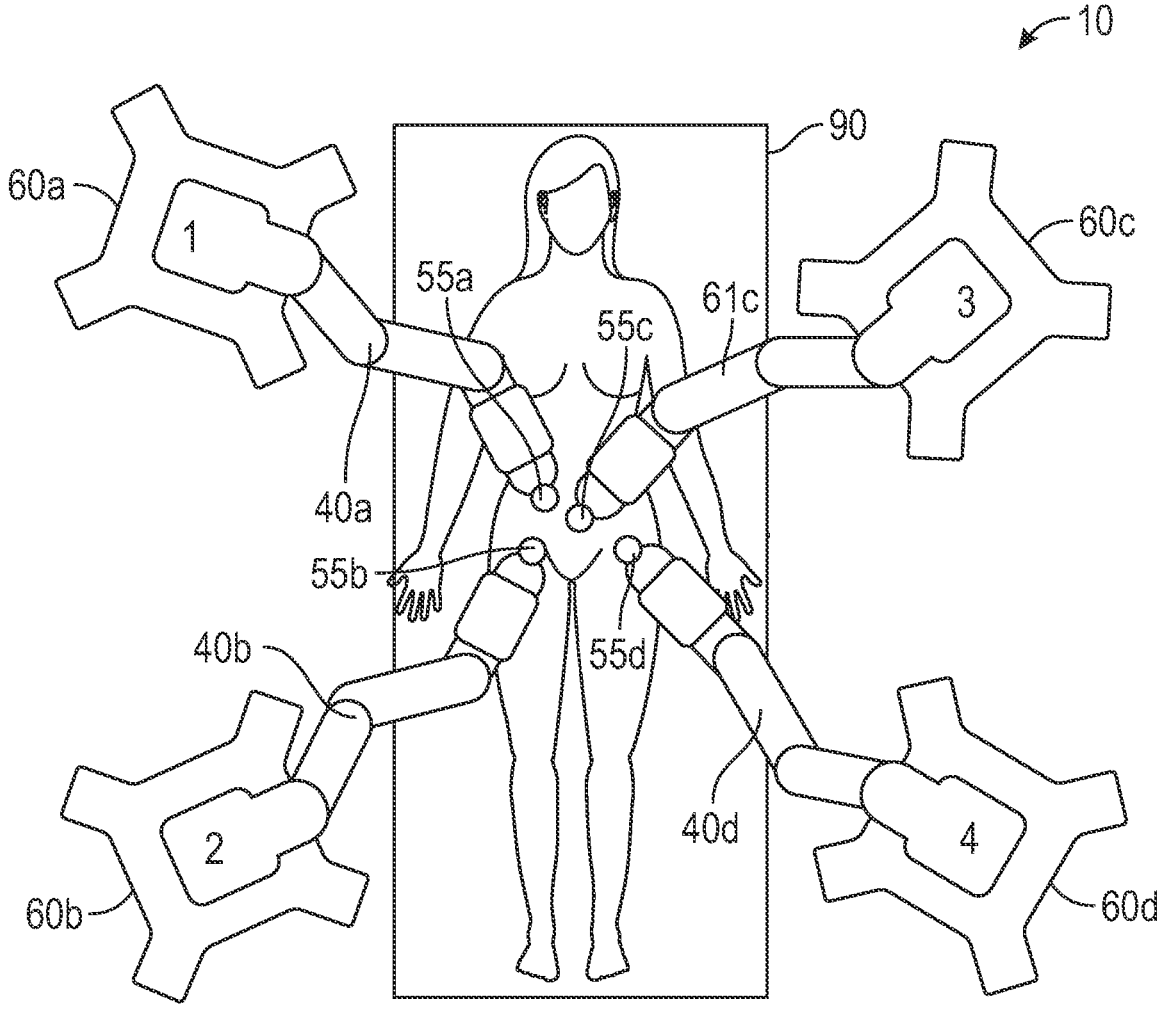
FIG. 9 is a plan schematic view of movable carts of FIG. 1 positioned about a surgical table according to an aspect of the present disclosure.

With reference to FIG. 8, another method for verifying length of the access port 55 includes at step 400 setting up the system as shown in FIG. 9. The methods of FIGS. 7 and 8 may be implemented as software instructions executable by any of the controllers of the system 10 (e.g., controllers 21a, 31, 41a, etc.).

In embodiments, the surgical robotic system 10 is setup around a surgical table 90. (See FIG. 9.) The system 10 includes movable carts 60a-d, which may be numbered "1" through "4." During setup, each of the carts 60a-d are positioned around the surgical table 90. Position and orientation of the carts 60a-d depends on a plurality of factors, such as placement of a plurality of access ports 55a-d, which in turn, depends on the surgery being performed. Once the port placement is determined, the access ports 55a-d are inserted into the patient, and carts 60a-d are positioned to insert instruments 50 and the endoscopic camera 51 into corresponding ports 55a-d.

As described above, different types of access ports 55a-d may be used. In particular, access ports having different dimensions (e.g., diameter and lengths) may be used. The access port 55a may be a standard length access port having a length of from about 100 mm to about 200 mm, whereas the access port 55b may be a long length port, having a length of 200 mm or above. Port diameter may be different for different ports, and may be from about 5 mm to about 15 mm.

As step 402, the system 10 provides a prompt to the user (e.g., via a GUI on the first display 32) asking whether there are any long ports that are being used. The prompt may be a pop-up query with "YES" and "NO" responses. If the response is "YES", then the system 10 sets all of the access ports 55a-d as long length ports at step 404. If the response is "NO" then the system 10 sets all of the access ports 55a-d as standard length ports at step 406. In embodiments, the system 10 may provide individual prompts for each of the access ports 55a-d and receive responses for each prompt and access port.

During operation of the robotic arms 40a-d and the instruments 50 in response to user inputs at surgeon console 30, the system 10 monitors whether the user is attempting to operate the instrument 50 beyond a virtual boundary of a standard length access port. The system 10 may store in memory or calculate for different types of access ports 55a-d a virtual boundary, e.g., a first 3D space reachable by the instrument 50 when operated through a standard access port and a second 3D space reachable by the instrument 50 when operated through a long length access port. The second 3D space may be smaller than the first 3D space.

At step 407, the system 10 confirms the user's response that all access ports are of long lengths. The system 10 monitors user's operation of the instrument 50. In particular, the system 10 counts the number of times the user attempted to operate the instrument 50 beyond the virtual boundary and whether each of the attempts (i.e., movement and/or position beyond the virtual boundary) exceeded a predetermined time limit. The number of attempts threshold may be 2 or above, and the time threshold may be about 2 seconds or above.

If the system 10 determines that the instrument 50 was operated outside the virtual boundary (i.e., number of attempts longer than the time threshold is larger than the attempt threshold), then the system 10 proceeds to step 412, which prompts the user with a second prompt at step 412 to confirm that the user correctly answered the first prompt at step 402 since the usage of the instrument 50 as monitored by the system 10 contradicts user's initial classification of the access port (i.e., stating the access port is long but the movement confirms that the access port is standard). The prompt asks the user (e.g., via the GUI on the first display 32) whether the access port is a standard or long type access port. The prompt may be a "YES" or "NO" query or a query asking the user to identify the type (e.g., "STANDARD" or "LONG"). Based on the response to the prompt, the system 10 sets the access port type as "standard" at step 414 or as "long" at step 416. If the system 10 determines that the instrument 50 was operated within the virtual boundary, then the process ends at step 410.

During the surgical procedure, the system 10 also continuously monitors detachment and/or reattachment of access ports 55a-d at step 408. If all of the access ports 55a-d that were present during setup of the system 10 remain through the duration of the procedure, then the process ends at step 410. If at any time a port is reattached or a new access port is attached, the system 10 detects the attachment and prompts the user with a second prompt at step 412. The prompt asks the user (e.g., via the GUI on the first display 32) whether the newly attached access port is a standard or long type access port. The prompt may be a "YES" or "NO" query or a query asking the user to identify the type (e.g., "STANDARD" or "LONG"). Based on the response to the prompt, the system 10 sets the access port type as "standard" at step 414 or as "long" at step 416.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a robotic arm configured to support an access port and an instrument having an end effector inserted into the access port;
a surgeon console configured to detect user activity;
a controller configured to:
measure an insertion distance of the instrument within the access port;
detect the user activity; and
prevent actuation of the end effector in response to detection of the user activity while the insertion distance is less than a threshold distance, wherein the threshold distance corresponds to a length of the access port to prevent articulation of the end effector within the access port.

2. The surgical robotic system according to claim 1, wherein the surgeon console includes a hand controller having a gimbal assembly and a finger sensor.

3. The surgical robotic system according to claim 2, wherein the user activity includes at least one of contacting the finger sensor or rotating the hand controller about the gimbal assembly.

4. The surgical robotic system according to claim 3, wherein the surgeon console includes a head tracking device configured to detect at least one of head position or eye direction.

5. The surgical robotic system according to claim 4, wherein the user activity includes at least one of head or eye pointing toward the surgeon console.

6. The surgical robotic system according to claim 5, further comprising a display.

7. The surgical robotic system according to claim 6, wherein the controller is further configured to output a confirmation query on the display in response to detection of the user activity and the insertion distance being less than the threshold distance.

8. The surgical robotic system according to claim 7, wherein the display is a touchscreen, and a response to the confirmation query includes touching the touchscreen.

9. The surgical robotic system according to claim 8, wherein the head tracking device is configured to detect a head nod as the response to the confirmation query.

10. The surgical robotic system according to claim 1, wherein the controller is further configured to:
enable actuation of the end effector in response to a confirmation that a length of the access port is less than the threshold distance or the length of the insertion distance of the instrument exceeding the threshold; and
modify the threshold based on the confirmation.

11. A method for controlling a surgical robotic system, the method comprising:
measuring an insertion distance of an instrument having an end effector into an access port, the instrument and the access port supported by a robotic arm;
monitoring user activity at a surgeon console; and
outputting an alert on a surgeon console and preventing actuation of the end effector in response to detection of the user activity while the insertion distance is less than a threshold distance, wherein the threshold distance corresponds to a length of the access port to prevent articulation of the end effector within the access port.

12. The method according to claim 11, wherein the surgeon console includes a hand controller having a gimbal assembly and a finger sensor.

13. The method according to claim 12, wherein detecting the user activity includes detecting at least one of contacting the finger sensor or rotating the hand controller about the gimbal assembly.

14. The method according to claim 13, wherein detecting the user activity includes tracking at least one head position or eye direction at a head tracking device of the surgeon console.

15. The method according to claim 14, wherein tracking at least one of the head position or the eye direction the user activity includes detecting at least one of head or eye pointing toward the surgeon console.

16. The method according to claim 15, further comprising displaying a graphical user interface on a display.

17. The method according to claim 16, further comprising outputting a confirmation query on the display in response to detection of the user activity and the insertion distance being less than the threshold distance.

18. The method according to claim 17, further comprising:

receiving a response to the confirmation query at a touchscreen of the display; and detecting a head nod as the response to the confirmation query at the head tracking device.

19. The method according to claim 11, further comprising enabling actuation of the end effector at a controller in response to a confirmation that a length of the access port is less than the threshold distance.

20. A method for controlling a surgical robotic system, the method comprising:

measuring an insertion distance of an instrument having an end effector into an access port, the instrument and the access port supported by a robotic arm;

detecting user input at a surgeon console; and preventing actuation of the end effector in response to detection of the user input while the insertion distance is less than a threshold distance, wherein the threshold distance corresponds to a length of the access port to prevent articulation of the end effector within the access port.

\* \* \* \* \*